United States Patent [19]

Grimm

[11] 4,279,597
[45] Jul. 21, 1981

[54] CHUCK ASSEMBLY FOR DENTAL HANDPIECES

[75] Inventor: Phillip R. Grimm, Arlington Heights, Ill.

[73] Assignee: American Hospital Supply Corporation, Evanston, Ill.

[21] Appl. No.: 74,720

[22] Filed: Sep. 12, 1979

Related U.S. Application Data

[63] Continuation-in-part of Ser. No. 885,290, Mar. 10, 1978, abandoned.

[51] Int. Cl.³ .............................................. A61C 1/14
[52] U.S. Cl. ...................................... 433/129; 279/50
[58] Field of Search ............... 433/129, 124, 127, 132; 279/43, 50, 51, 57, 58

[56] References Cited

U.S. PATENT DOCUMENTS

| 351,821 | 11/1886 | Weber | 433/129 |
|---|---|---|---|
| 382,672 | 5/1888 | Williams | 433/129 |
| 3,627,339 | 12/1971 | Burweger | 279/50 |
| 3,637,050 | 1/1972 | Hoffmeister | 433/132 |
| 3,798,776 | 3/1974 | Lentine et al. | 433/129 |
| 3,888,008 | 6/1975 | Lake et al. | 433/129 |
| 4,089,115 | 5/1978 | Heil et al. | 433/124 |

FOREIGN PATENT DOCUMENTS 684569  3/1965  Italy .......................................... 433/127

Primary Examiner—Gene Mancene
Assistant Examiner—John J. Wilson
Attorney, Agent, or Firm—Tilton, Fallon, Lungmus

[57] ABSTRACT

An improved positive-grip chuck assembly, particularly suitable for use with high-speed air-driven dental handpieces, in which a tubular chuck has a radially-flexible bur-clamping section provided with an external shoulder, and the bore in which the chuck is received has an internal shoulder engagable with the external shoulder of the bur clamping section of the chuck to flex the bur-clamping section inwardly and to hold the same in a constricted condition for securely gripping the midportion of the shank of a dental bur. Piloting contact is made between the chuck and bur along circumferential zones spaced axially from the bur-clamping zone, and the rotor surrounds and braces the chuck portion defining the lower pilot zone to prevent distorting forces applied to the tip of the bur from being propagated to the bur-clamping zone.

9 Claims, 8 Drawing Figures

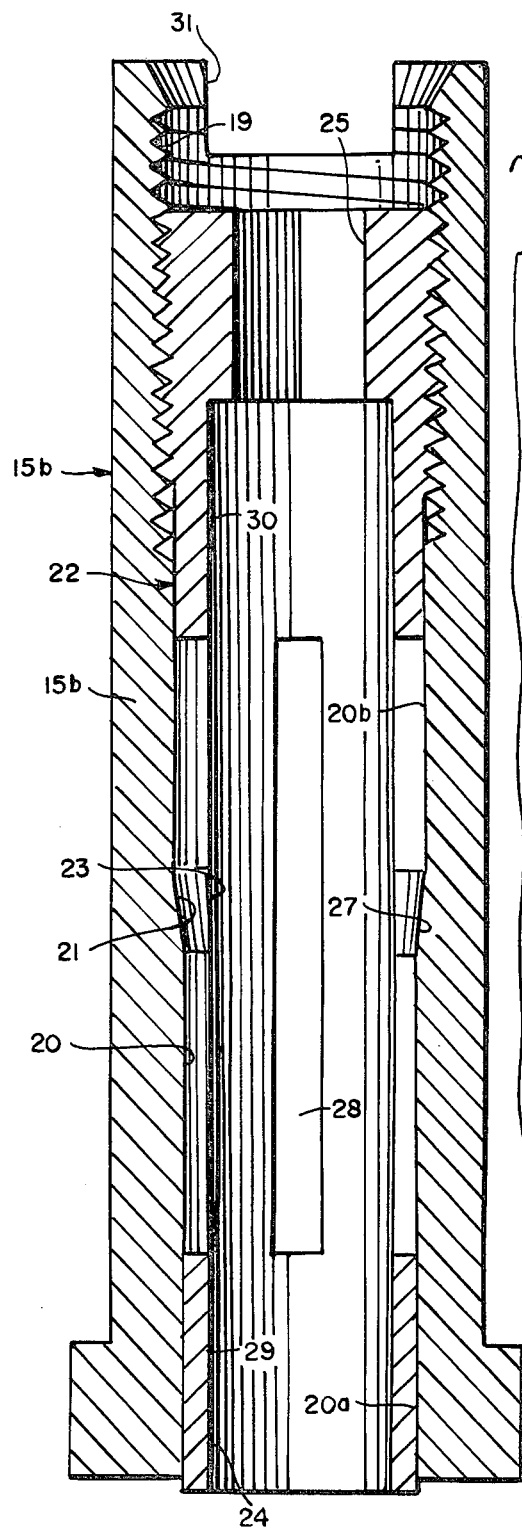
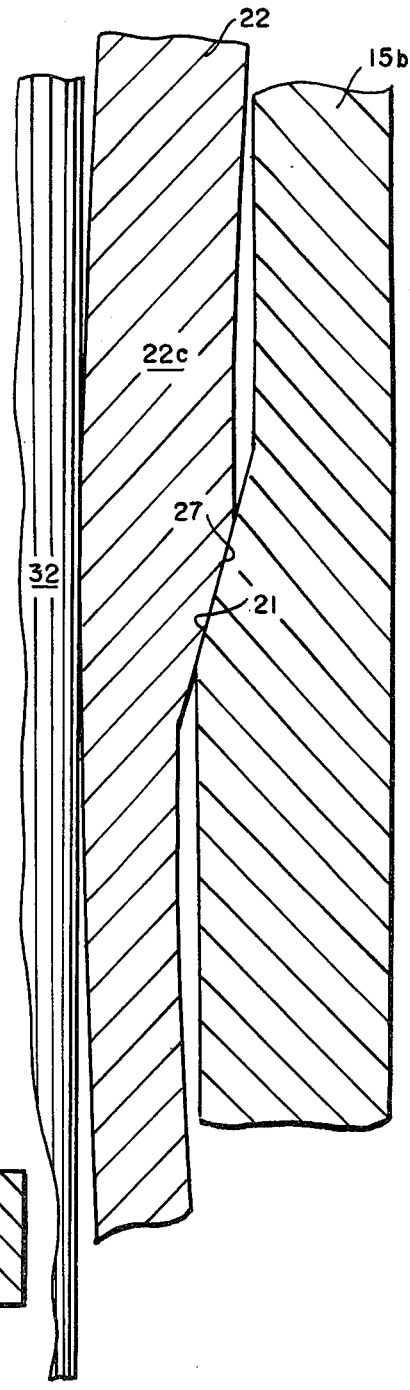
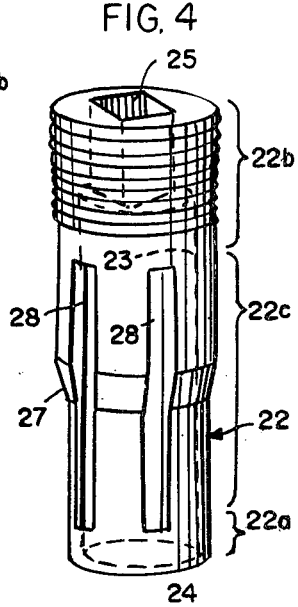
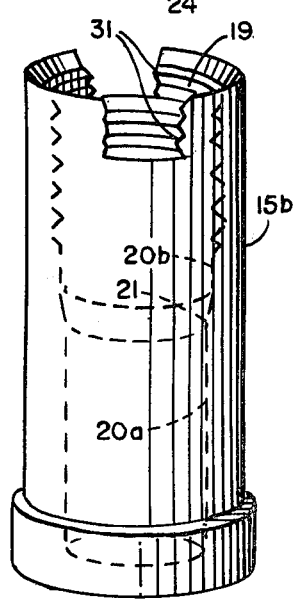

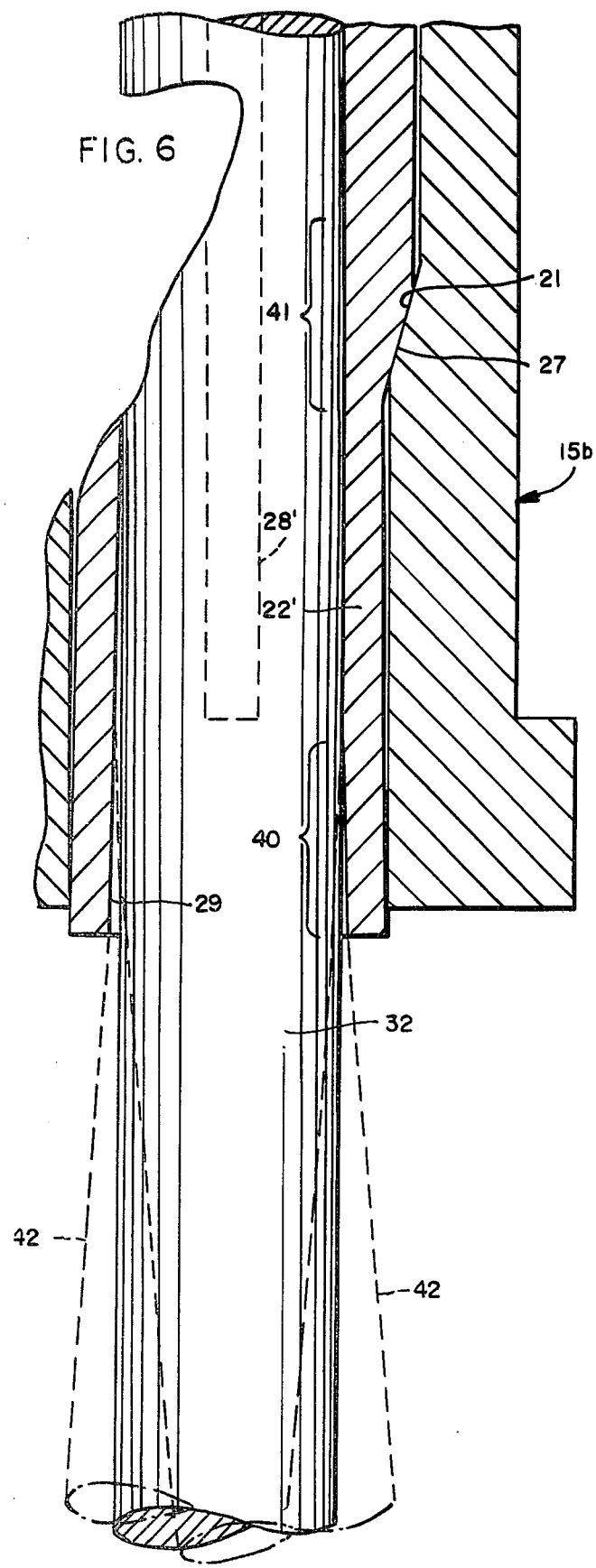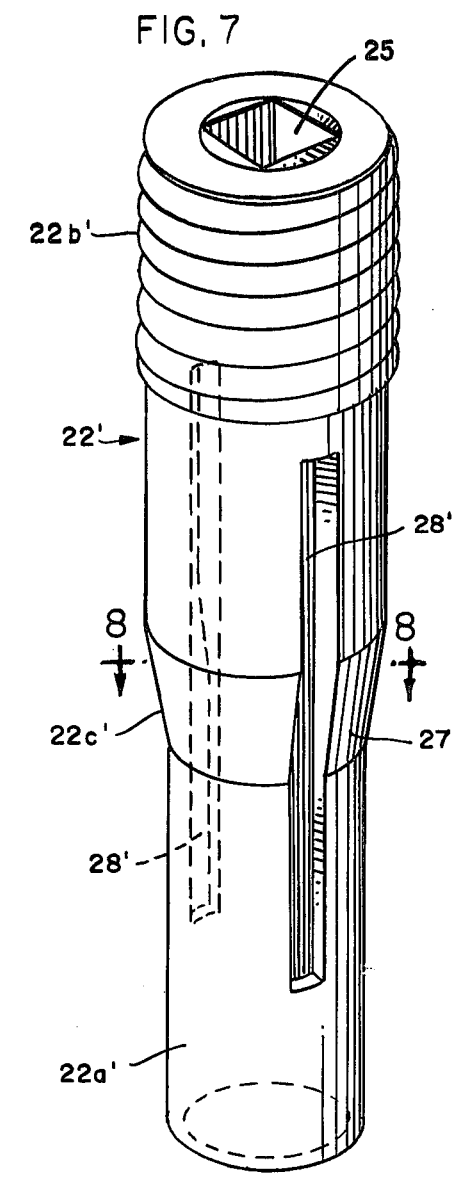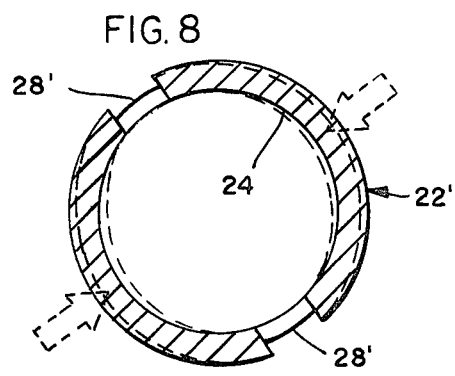

CHUCK ASSEMBLY FOR DENTAL HANDPIECES

RELATED APPLICATION

This application is a continuation-in-part of my co-pending application Ser. No. 885,290, filed Mar. 10, 1978, and now abandoned.

BACKGROUND

The chucks used for releasably holding burs in high-speed dental handpieces have chucking actions that can be generally categorized as falling within two main groups. The first group includes collet chucks which are normally wrench operated and which are threadedly mounted within the rotary members (usually bur tubes) of the handpieces so that the terminal gripping fingers of the chucks are forced to close or allowed to open depending on whether the wrenches are rotated in one direction or the other. The second group includes spring-gripped chucks which depend on the resilience or spring characteristics of the chucks for bur retention. While efforts have been made to develop a fully satisfactory chuck which overcomes certain disadvantages that have come to be associated with chucks of these types, such efforts have not been entirely successful.

Wrench operated chucks, whether of the pull-to-tighten or push-to-tighten variety, tend to undergo bur "walkout" or rejection from high-speed turbine-driven dental handpieces during conditions of extremely heavy cutting, particularly in tenacious types of material such as gold alloys and some silver amalgams under which the cutting dynamics are severe. The problem is characteristically associated with high-speed handpieces—that is, handpieces which develop rotational speeds in excess of 100,000 revolutions per minute and, more particularly, speeds of the order of 200,000 to 500,000 revolutions per minute. Handpieces capable of such high speed operation are invariably of the air turbine type, in contrast to electrically-powered handpieces. Tests have shown that axial walkout may occur even without accompanying torsional slippage of the bur. Although the axial walkout problem is a serious one which has existed for a number of years, the precise reasons why the problem occurs do not appear to have been fully known, or at least have not been fully analyzed and reported in any known technical literature.

A variation of the push-to-tighten chuck is a double-ended type, that is, a chuck with spring fingers at opposite ends, cooperatively associated with a separate nut. While advantages in eliminating or reducing bur walkout can generally be anticipated with this type of chuck, there are disadvantages which include the possibility of the nut loosening during cutting, thereby presenting the danger of the chuck, bur, and/or tightening nut releasing during handpiece operation. U.S. Patents illustrative of double-ended chucks are Nos. 3,619,904 and 3,488,850.

While spring grip type chucks are known to be more resistant to bur walkout, they are commonly associated with other troublesome disadvantages. Since spring action, in contrast to a positive clamping action, is responsible for bur retention, problems of durability, dependability, wear and fatigue are often associated with spring grip chucks. Also, problems are often encountered in attaching or removing burs. In the use of a spring grip chuck, the bur is normally removed by utilizing a small diameter push rod which the operator must direct with a force strong enough to overcome the frictional forces exerted by the spring. Conversely, in order to insert a bur, the bur must generally be placed against a soft brass or plastic slug so that it can be pushed into place without damage to the cutting surface of the bur. Major disadvantages of spring grip chucks have resided in the fact that it is often difficult and dangerous for operators to apply sufficient force to overcome the springs for bur insertion and removal without damaging the burs, the handpieces, or both. U.S. Patents illustrative of spring grip chucks are Nos. 2,963,519, 3,088,745, 3,255,527, 3,321,209, 3,426,429, 4,021,919 and 4,012,841.

Other U.S. patents showing wrench-operated collet chucks are Nos. 3,325,899, 3,496,638, 3,813,782 and 3,888,008.

SUMMARY

This invention is concerned with a chuck assembly which provides the advantages of both spring-grip and wrench-operated chucks without the aforementioned disadvantages of prior chuck constructions. More specifically, it is an object to provide an improved chuck assembly which is relatively simple in construction, is wrench-operated for positive gripping action, is capable of withstanding the substantial torsional forces generated when such a chuck is tightened to grip a dental bur, and is remarkably free of bur walkout problems even when the high-speed handpiece is used to cut through gold alloys, amalgams, and other tenacious materials. A further object is to provide a chuck assembly which is durable, does not wear readily or break easily and is field replaceable. In addition to its other advantages, the chuck assembly is easily operated to release and secure a bur and, in contrast to at least some conventional wrench-operated chuck assemblies, does not tend to score, gouge, or otherwise damage the surface of a bur shank during normal use.

The chuck assembly consists essentially of two main elements: a rotor having a bore, and a chuck received within that bore. The term "rotor" is used herein to refer to the rotatably mounted member of a high-speed turbine-driven dental handpiece. Ordinarily, the rotor will either be the turbine itself or a bur tube secured within that turbine. While the invention might be utilized with dental handpieces other than turbine-driven high-speed handpieces, the problem of bur walkout is not encountered with low-speed handpieces and, therefore, a major benefit of the invention would not be realized.

The chuck is formed in one piece, is tubular, and defines a bore for receiving the shank of a dental bur. The chuck includes an integral bur-clamping or bur-gripping section disposed intermediate the length of the chuck (and of the rotor's bore), such section being defined by an external shoulder or bearing surface and being capable of flexing radially inwardly to clamp the mid-portion of the shank of a dental bur extending therethrough.

The external shoulder of the bur-gripping section is engagable with an internal shoulder within the bore of the rotor so that as the shoulders are urged axially into forceful engagement the bur-gripping section of the chuck will flex radially inwardly to engage and grip the mid-portion of the bur shank.

Above and below the bur-gripping section—that is, spaced from opposite ends of that section—are elongated pilot passages which snugly but slidably receive portions of the bur shank in zones spaced axially from the bur-gripping section. The rotor extends substantially the full length of the chuck and includes a lower end portion which surrounds and braces the lower pilot section of the chuck to prevent flexing forces directed against the bur during operation from being propagated beyond the lower pilot zone to the bur-gripping zone. The result is a construction which is positive in operation and remarkably free of bur walkout or ejection in use.

In the disclosed embodiment the pilot sections and bur-clamping or bur-gripping sections of the chuck are integrally formed. The clamping section is disposed intermediate the length of the chuck and its radial deformability is achieved by providing a plurality of openings or slots in circumferentially-spaced positions about the chuck. In the best mode presently known for practicing the invention, the chuck is provided with just two such slots arranged in diametric opposition. Not only does the two-slot construction perform at least as effectively as constructions having greater numbers of slots, but the two-slot construction achieves such results while providing superior torsional rigidity. Such torsional rigidity is particularly important because of the threaded interconnection between the chuck and rotor and the fact that the chuck is tightened by rotating it within the rotor until the parts are in such forceful engagement that the intermediate slotted section of the chuck is deformed or flexed radially inwardly to grip the bur. Such forceful engagement between the chuck and rotor imposes considerable torsional strain on the longitudinally-elongated and arcuate web portions spaced by the slots of the chuck. In addition to its superior strength and performance characteristics, the two-slot chuck construction has the advantages of being easier and less-costly to manufacture.

Other features of the structure and its operation, and other advantages and objects of the invention, will become apparent from the specification and drawings.

THE DRAWINGS

FIG. 3 is a further enlarged longitudinal sectional view of the chuck assembly.

FIG. 4 is an exploded perspective view of the components of that assembly.

FIG. 5 is a greatly enlarged fragmentary and somewhat exaggerated sectional view depicting the deformation of the intermediate portion of the chuck which results in bur retention.

FIG. 6 is an enlarged fragmentary and somewhat exaggerated longitudinal sectional view of a chuck and rotor assembly constituting a preferred embodiment of the invention.

FIG. 7 is a perspective view of the chuck of FIG. 6.

FIG. 8 is a cross sectional view taken along lines 8—8 of FIG. 7.

DETAILED DESCRIPTION

Figure 2:
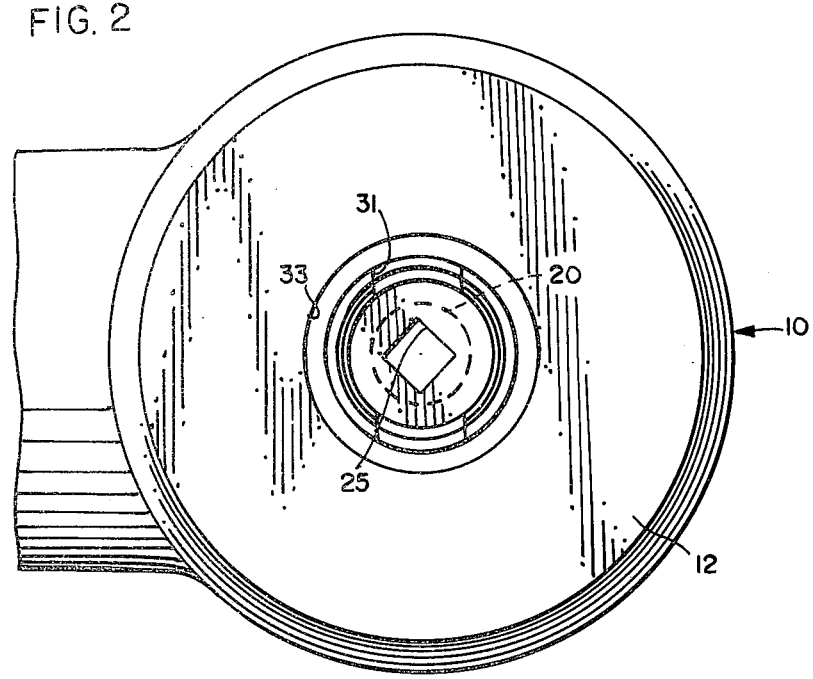
FIG. 2 is a top plan view of the handpiece of FIG. 1.
Figure 1:
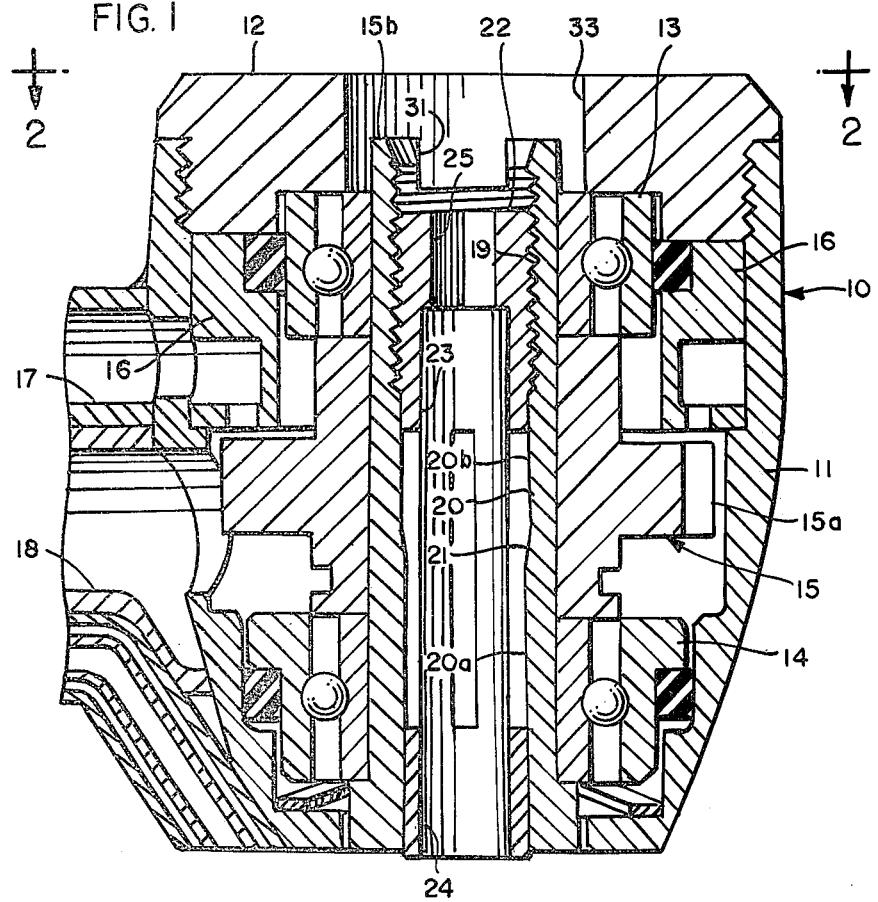
FIG. 1 is an enlarged sectional view of the head portion of a dental handpiece equipped with the chuck assembly of this invention.

Referring to FIGS. 1 and 2, the numeral 10 generally designates a dental handpiece having a housing 11 and a cap 12 threadedly secured to the housing at the upper end thereof. The handpiece selected for illustration is an air-driven handpiece having a pair of ball bearing assemblies 13 and 14 supporting rotor 15 for rotation within the chamber defined by the housing. The rotor includes driving means in the form of turbine 15a and bur tube 15b. The turbine depicted in FIG. 1 is an axial-flow turbine which is driven by air discharged from stator 16, the stator in turn receiving drive air supplied by drive air passage 17. The bulk of the air discharged from the turbine is exhausted through discharge passage 18.

The rotor tube or bur tube 15b is provided with internal threads 19 at the upper portion of its axial bore 20. A sloping internal shoulder 21 is located intermediate the upper and lower ends of the bore. Shoulder 21 defines the boundary between two sections of the bore 20 of different diameter, the lower section 20a adjacent the bur-receiving end of the handpiece having smaller diameter than upper section 20b.

As shown most clearly in FIGS. 3 and 4, a tubular chuck 22 is disposed within the rotor tube 15b. The chuck has a bore 23 extending therethrough, the lower cylindrical portion 24 of the bore defining a socket for receiving the shank of a bur, and the upper portion 25 being of non-circular cross section (preferably square) to define a socket for receiving a suitable wrench (not shown).

Although the chuck of FIGS. 1–5 is formed of a single piece of material, it may conveniently be considered as being composed of a plurality of sections or portions, namely, a lower end portion 22a, an upper end portion 22b, and an intermediate portion 22c. The wall of the intermediate portion 22c is provided with an external shoulder adapted to engage the internal shoulder 21 of the rotor tube when the parts are assembled as illustrated in FIG. 3. The upper portion 22b is externally threaded, the threads of that portion mating with the internal threads of the rotor tube. Because of the downwardly and inwardly sloping configuration of the shoulders, the intermediate portion 22c of the chuck is pressed radially inwardly when the chuck is screwed downwardly to urge shoulders 21 and 27 into forceful engagement with each other. Since the dimensional difference between the outside diameter of a bur shank and the inside diameter of bore portion 24 is small, and since such parts are manufactured to close tolerance, only slight inward flexing or deformation of the wall of the intermediate bur-clamping portion or section 22c is required in order to grip the bur. To promote effective flexure without the need for applying excessive twisting force to rotate the chuck 22 within the rotor tube 15b after the sloping shoulders have made contact with each other, openings or slots 28 are formed in the wall of the intermediate bur-clamping portion 22c. The openings or slots are circumferentially spaced and, in the embodiment depicted in FIGS. 1–5, are longitudinally elongated, running the full length of the intermediate bur-clamping portion 22c.

Where autoclavability is required or desired, the material of choice for the chuck as well as other parts of the handpiece is believed to be stainless steel. The slotted chuck construction shown in the drawings is intended to be fabricated out of stainless steel although it is believed apparent that other materials having the necessary properties of flexibility, strength, and durability might be used.

It should be observed that above and below the bur-clamping section 22c of the chuck are upper and lower portions 22b and 22a, respectively, which define upper and lower pilot guide passages 29 and 30. In the illustration given, such passages are portions of the cylindrical section 24 of the bore 23. As previously indicated, bore portion 24, and especially pilot passage sections 29 and 30 of that portion of the bore, are only slightly larger in diameter than the shank of the bur to be received therein. The relationship has been referred to as a snug but slidable fit; in technical terms, the spacing should be as small as manufacturing tolerances permit, hopefully of the order of magnitude of 0.0005 of an inch. By reason of the close but slidable fit between the shank of a bur and the upper and lower pilot passages at each end of the chuck's bur-gripping section, and the bracing effect of the surrounding rotor tube 15, particularly the bracing effect of that rotor tube on the lower piloting portion of the chuck, concentricity between the bur and rotor may be achieved and maintained. The gripping of the shank of the chuck in an intermediate zone disposed between and spaced from the upper and lower pilot zones, and the bracing of those pilot zones, are believed to be responsible for the absence of bur walkout during operation of handpiece 10.

The wrench used for adjusting chuck 22 is not shown because it forms no direct part of the present invention and because such wrenches are widely used and well known. Reference may be had to U.S. Pat. Nos. 3,235,899 and 3,888,008 for wrenches adaptable for use with the chuck assembly disclosed herein. The square socket 25 has already been described for the purpose of coupling the wrench to chuck 22. Notches 31 (FIG. 4) are formed in the upper end of rotor tube 15b for the purpose of coupling the wrench to that tube, it being understood that in the operation of either loosening or tightening the chuck, one part (the chuck or the rotor tube) must be rotated while the other part (the rotor tube or the chuck) must be held stationary.

FIG. 5 depicts in enlarged and greatly exaggerated fashion the cooperative relationship between the parts during operation of the chuck assembly. As the chuck 22 is screwed downwardly to force external shoulder 27 into camming engagement with internal shoulder 21 of rotor tube 15b, the deformable intermediate portion 22c of the chuck is flexed or deformed radially inwardly into tight gripping engagement with the shank 32 of a dental bur. It will be observed that the wall of the intermediate portion is flexed radially into a curved configuration and that clamping contact between the chuck and the bur occurs along a zone of substantial longitudinal extent. The length of that zone contrasts sharply with the line of contact or biting action characteristic of conventional collet chucks. The longitudinal curvature of the deformed intermediate portion 22c not only eliminates any appreciable scoring or marring of the surface of shank 22 but, at the same time, produces an extraordinarily effective gripping action which is highly resistant to bur walkout and slippage.

The one-piece chuck may be easily removed by simply unthreading it from the rotor tube 15b and extracting it through the enlarged opening 33 in the cap of the hand-piece. Therefore, should cleaning of the chuck be desired, or should replacement become necessary, such operations may be readily performed by the dentist or his assistant. Since the lower section 20a of the bore of the rotor tube is smaller in diameter than the upper section 20b, and since the lower portion 22a of the chuck is likewise smaller than the upper portion 22b, there is no possibility that during handpiece operation the chuck might somehow become loosened and released from the lower end of the rotor tube.

In the embodiment of FIGS. 1-5, the unitary chuck 22 is provided with four circumferentially-spaced slots 28. Chuck 22' of FIGS. 6-8 is substantially identical to chuck 22 except that only two diametrically-opposing slots 28' are provided. The rotor and handpiece in which the chuck 22 is mounted may be identical to the parts already described; therefore, in FIGS. 6-8 the same numerals are used to designate elements that do not differ from those previously described.

The effectiveness of the embodiment of FIGS 6-8 appears to confirm what applicant has theorized to be the mechanics of bur walkout in high speed (200,000 to 500,000 or more rpm) dental handpieces. In a conventional wrench-operated chuck, spring fingers at the chuck's lower end are forced into tight engagement with the shank of a dental bur. Slight flexure of the exposed shank of the bur below the jaws in response to laterally directed forces against the tip of the bur tends to cause a biting and pivoting action to take place along an arc of movement opposite from the point of applied force, accompanied by a slight sliding or slipping action along that arc of movement on the same side as the applied force. With each revolution of the flexed bur, any given point on the surface of that bur engaged by a jaw of a conventional chuck alternately pivots against that jaw and then, 180° later, when the point of contact generally faces the point of applied force, may slip slightly downwardly from the jaw. For reasons not fully understood, walkout has not been found to be a significant problem with low or medium speed (i.e., under 200,000 rpm) handpieces. However, with high-speed handpieces, such alternate biting, pivoting, and sliding action may result in rapid walkout at some risk to dentist, patient, or both.

The characteristic of both of the embodiments disclosed herein is that piloting of the bur at the lower end of the chuck, braced by the bur tube, occurs a substantial axial distance from the area in which the bur is gripped and held. In FIG. 6, the numeral 40 generally designates the zone or area of piloting action at the lower end of chuck 22', whereas numeral 41 indicates the zone or area of forceful gripping contact between the chuck and a bur 32. The two zones 40 and 41 are spaced axially apart a substantial distance. When flexing movement of the lower portion of a bur takes place (such movement is shown in exaggerated form by broken lines 42 in FIG. 6), contact between the chuck 22' and bur 32 in pilot zone 40, coupled with the reinforcement of the chuck's lower end provided by the surrounding bur tube 15b, prevent the flexing action of the bur tube from being transmitted or propagated upwardly to the bur-clamping zone 41. A primary reason why bur walkout is so effectively prevented is believed to reside in the spacing of the two zones and the external bracing of the chuck's lower end by the rotor tube 15b, thereby isolating the gripping zone 41 from flexing action of the bur occasioned by lateral forces generated when the tip of the bur is forced against a work object.

Spacings and deformations are exaggerated in FIGS. 6 and 8 for illustrative purposes. When the intermediate bur-gripping portion of the chuck is cammed inwardly into tight gripping contact with a bur through forceful engagement between external and internal shoulders 27 and 21, respectively, the side walls or web portions of the chuck on opposite sides of slots 28' are urged inwardly as indicated by broken lines in FIG. 8. The bur is therefore tightly gripped along diametrically-opposing surface portions. It has been found that effective gripping action takes place even though the areas of forceful contact are diametrically-disposed rather than being spaced at three or more points about the circumference of the bur, and it is believed that such effectiveness arises to a considerable extent because of the braced piloting of the bur at the lower end of the chuck in a zone 40 spaced axially from gripping zone 41.

Since only two slots 28' are provided, chuck 22' has outstanding torsional rigidity and is better able than chucks having a greater number of slots to withstand the substantial twisting forces that develop when such a chuck is tightened or loosened by a wrench. Also, to the extent that formation of a pair of slots requires less machining, and simpler machining procedures, than the formation of a greater number of slots, the chuck of FIGS. 6–8 is advantageous in terms of ease and lower costs of manufacture.

While in the foregoing, embodiments of the invention have been disclosed in considerable detail for purposes of illustration, it will be understood by those skilled in the art that many of these details may be varied without departing from the spirit and scope of the invention.

I claim:

1. A positive-bur-gripping chuck assembly for a high-speed dental handpiece generally operable at rotational speeds in excess of 100,000 rpm, comprising a rotor having a bore therethrough and having upper, lower, and intermediate sections; said intermediate section providing an internal shoulder within said bore; a tubular chuck received within said bore and having an upper end portion, a deformable intermediate portion, and a cylindrical lower end portion; said upper section of said rotor and said upper end portion of said chuck threadedly engaging each other; means provided by said chuck for engaging a wrench for rotating and thereby axially displacing said chuck within said rotor bore; said chuck having a generally cylindrical bore therethrough for receiving the shank of a dental bur; said deformable intermediate portion of said chuck being provided with an external shoulder engagable with said internal shoulder of said rotor to cam said deformable intermediate portion inwardly into tight clamping engagement with the shank of a dental bur when said shoulders of said chuck and rotor are urged axially into engagement with each other; said lower portion of said chuck defining a pilot zone for snugly but slidably engaging the shank of a bur at a substantial axial distance from said shoulders; and means provided by said rotor for surrounding and bracing said pilot zone of said chuck to prevent forces directed against said bur from being propagated beyond said pilot zone into the zone of clamping engagement with a dental bur.

2. The assembly of claim 1 in which said deformable intermediate portion of said chuck is provided with a plurality of circumferentially-spaced axially-elongated slots terminating adjacent said upper and lower portions of said chuck.

3. The assembly of claim 1, in combination with a dental handpiece equipped with means for rotatably supporting and driving said rotor at a rotational speed in excess of 100,000 rpm.

4. The assembly of claim 1 in which said rotor is provided with notches at the upper section thereof for engagement with a chuck-adjusting wrench.

5. The assembly of claim 1 in which said upper portion of said chuck defines a second pilot zone for snugly but slidably engaging the shank of a bur at a substantial axial distance from said shoulders.

6. A positive bur-gripping chuck assembly for a high-speed dental handpiece generally operable at rotational speeds in excess of 100,000 rpm, comprising a rotor having a bore therethrough and having upper, lower, and intermediate sections; said intermediate section providing an internal shoulder within said bore; a tubular chuck received within said bore and having an upper end portion, an intermediate portion, and a cylindrical lower end portion; said intermediate portion having a pair of axially-elongated diametrically-opposing slots terminating at said upper and lower end portions, respectively, and defining a pair of flexible members therebetween; said upper section of said rotor and said upper end portion of said chuck threadedly engaging each other; means provided by said chuck for engaging a wrench for rotating and thereby axially displacing said chuck within said rotor bore; said chuck having a generally cylindrical bore therethrough for receiving the shank of a dental bur; said intermediate portion of said chuck being provided with an external shoulder engagable with said internal shoulder of said rotor to cam said flexible members inwardly into tight clamping engagement with the shank of a dental bur when said shoulders of said chuck and rotor are urged axially into engagement with each other; said lower portion of said chuck defining a pilot zone for snugly but slidably engaging the shank of a bur at a substantial distance from said shoulders; and means provided by said rotor for surrounding and bracing said pilot zone of said chuck below said slots to prevent forces directed against said bur from being propagated beyond said pilot zone into the zone of clamping engagement between said members and a dental bur.

7. The assembly of claim 6, in combination with a dental handpiece equipped with means for rotatably supporting and driving said rotor at a rotational speed in excess of 100,000 rpm.

8. The assembly of claim 6 in which said rotor is provided with notches at the upper end thereof for engagement with a chuck-adjusting wrench.

9. The assembly of claim 6 in which said upper end portion of said chuck defines a second pilot zone for snugly but slidably engaging the shank of a bur at a substantial axial distance from said shoulders.

* * * * *